(12) United States Patent
Humble

(10) Patent No.: US 8,840,610 B2
(45) Date of Patent: Sep. 23, 2014

(54) ELECTROSURGICAL SYSTEM INCLUDING ELECTROSURGICAL INSTRUMENT FOR LONGITUDINAL AND LATERAL TREATMENT

(75) Inventor: Robert C. Humble, Monmouthshire (GB)

(73) Assignee: Gyrus Medical Limited, Cardiff (GB)

( * ) Notice: Subject to any disclaimer, the term of this patent is extended or adjusted under 35 U.S.C. 154(b) by 908 days.

(21) Appl. No.: 13/016,298

(22) Filed: Jan. 28, 2011

(65) Prior Publication Data
US 2011/0196366 A1 Aug. 11, 2011

Related U.S. Application Data

(60) Provisional application No. 61/282,383, filed on Feb. 1, 2010.

(30) Foreign Application Priority Data

Feb. 1, 2010 (GB) .................................. 1001642.6

(51) Int. Cl.
A61B 18/12 (2006.01)
A61B 18/14 (2006.01)
A61B 18/16 (2006.01)
A61B 18/00 (2006.01)

(52) U.S. Cl.
CPC ...... *A61B 18/1482* (2013.01); *A61B 2018/1497* (2013.01); *A61B 2018/162* (2013.01); *A61B 2218/008* (2013.01); *A61B 2018/00922* (2013.01); *A61B 2018/1472* (2013.01)
USPC .......................................................... 606/41

(58) Field of Classification Search
USPC .............................................. 606/27, 34, 41
See application file for complete search history.

(56) References Cited

U.S. PATENT DOCUMENTS 5,009,656 A * 4/1991 Reimels ........................... 606/48
5,261,906 A * 11/1993 Pennino et al. .................. 606/46

(Continued)

FOREIGN PATENT DOCUMENTS

| EP | 0 895 756 | 2/1999 |
| WO | WO 95/08957 | 4/1995 |
| WO | WO 03/068095 | 8/2003 |

OTHER PUBLICATIONS

International Search Report and Written Opinion of the International Searching Authority issued in corresponding International Application No. PCT/GB2011/000100, mailed Aug. 11, 2011.

(Continued)

*Primary Examiner* — Michael Peffley
*Assistant Examiner* — Daniel Fowler
(74) *Attorney, Agent, or Firm* — Nixon & Vanderhye, PC

(57) ABSTRACT

An electrosurgical system is provided for the treatment of tissue, the system including an electrosurgical generator (1) for generating a radio frequency (RF) voltage, and an electrosurgical instrument (3) for the vaporization of tissue. The instrument (3) comprises an instrument shaft (10) having a longitudinal axis, and an electrode assembly at one end of the shaft. The electrode assembly comprises a tissue treatment electrode (11) and a return electrode (14, 25) electrically insulated one from another by means of an insulation member (12). The tissue treatment electrode (11) has an exposed surface (19) for treating tissue, the exposed surface of the tissue treatment electrode being laterally disposed on the instrument shaft (10), and being such that it presents a substantially planar face lying in a plane angled at between 120° and 177.5° to the longitudinal axis, with 0° and 180° being the proximal and distal directions of the longitudinal axis. The generator (1) is such that the magnitude of the RF voltage delivered to the tissue treatment electrode (11) is sufficient to cause tissue vaporization when the system is used for tissue treatment.

13 Claims, 7 Drawing Sheets

(56) References Cited

U.S. PATENT DOCUMENTS

Figure 1:
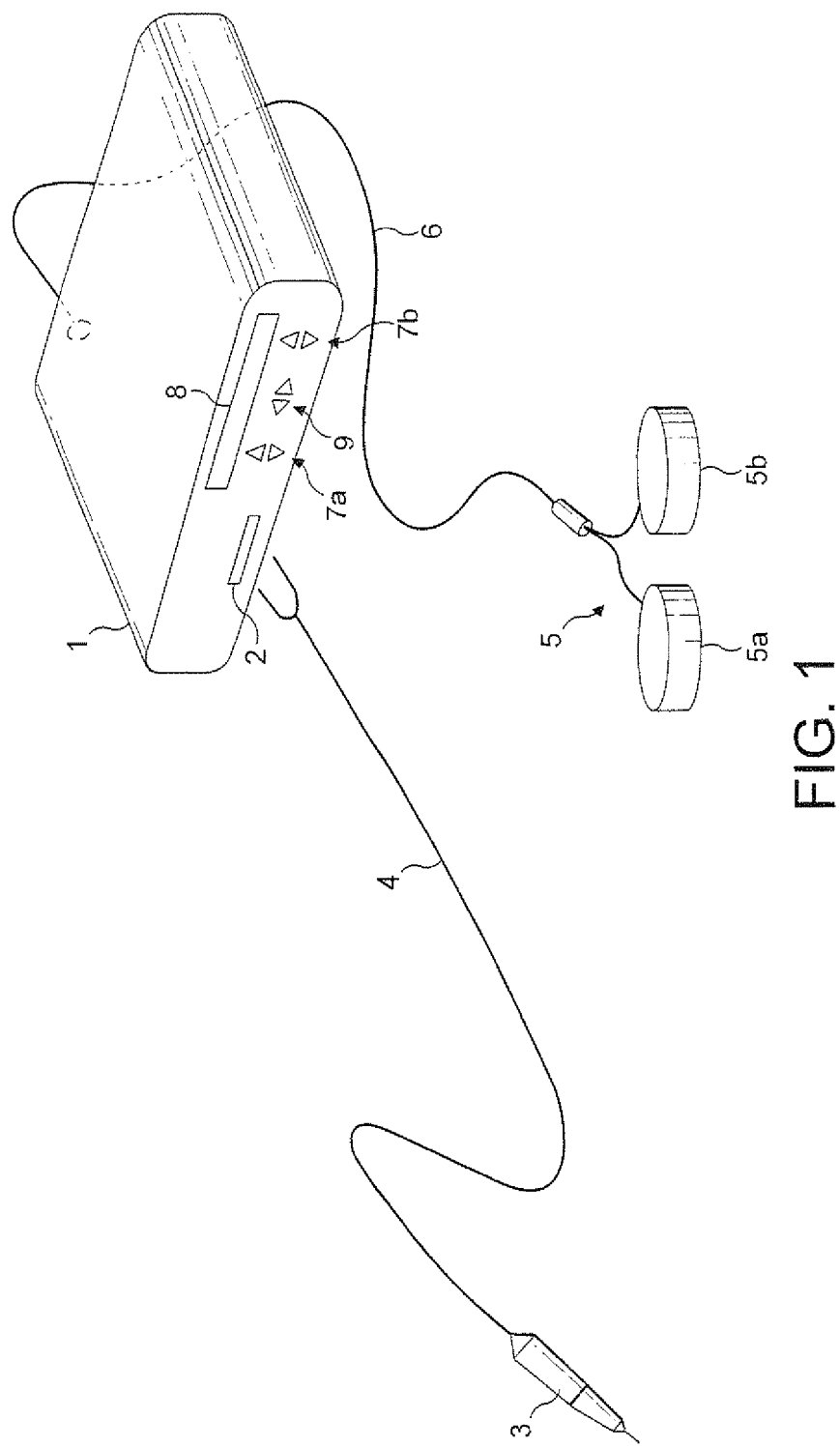

| | | |
|---|---|---|
| 5,441,499 A | 8/1995 | Fritzsch |
| 5,558,673 A * | 9/1996 | Edwards et al. .............. 606/41 |
| 5,697,909 A | 12/1997 | Eggers et al. |
| 5,741,250 A | 4/1998 | Garito et al. |
| 6,004,319 A | 12/1999 | Goble et al. |
| 6,091,995 A | 7/2000 | Ingle et al. |
| 6,168,593 B1 * | 1/2001 | Sharkey et al. .............. 606/34 |
| 6,293,942 B1 | 9/2001 | Goble et al. |
| 6,379,350 B1 * | 4/2002 | Sharkey et al. .............. 606/41 |
| 6,572,613 B1 | 6/2003 | Ellman et al. |
| 6,832,998 B2 | 12/2004 | Goble |
| 7,070,596 B1 | 7/2006 | Woloszko et al. |
| 8,333,761 B2 * | 12/2012 | Curtis ........................ 606/37 |
| 8,394,089 B2 * | 3/2013 | Curtis et al. ................ 606/37 |
| 2003/0130658 A1 | 7/2003 | Goble |
| 2003/0163178 A1 * | 8/2003 | Davison et al. ............ 607/101 |
| 2004/0153057 A1 * | 8/2004 | Davison ...................... 606/41 |
| 2005/0027235 A1 * | 2/2005 | Knudsen et al. ............ 604/20 |
| 2005/0283151 A1 | 12/2005 | Ebbutt |
| 2006/0052776 A1 | 3/2006 | Desinger et al. |
| 2010/0082026 A1 * | 4/2010 | Curtis ........................ 606/33 |

OTHER PUBLICATIONS

Search Report issued in Priority Application No. GB1001642.6, Date of Search: Jul. 23, 2010.

Partial International Search Report issued in corresponding International Application No. PCT/GB2011/000100, Date of Mailing: Apr. 15, 2011.

Search Report for corresponding Application No. GB 1001642.6, May 24, 2010.

* cited by examiner

ELECTROSURGICAL SYSTEM INCLUDING ELECTROSURGICAL INSTRUMENT FOR LONGITUDINAL AND LATERAL TREATMENT

This application claims priority to United Kingdom Application No. 1001642.6, filed 1 Feb. 2010 and claims the benefit of U.S. Provisional Application No. 61/282,383, filed 1 Feb. 2010, the entire contents of which are hereby incorporated by reference.

This invention relates to an electrosurgical system for the treatment of tissue. Such systems are commonly used for the vaporisation and/or coagulation of tissue in surgical intervention, most commonly in "keyhole" or minimally invasive surgery, but also in "open" surgery.

It is often the case that, during a surgical procedure, the surgeon is required to remove a first instrument and insert a second instrument, in order to achieve a particular tissue effect. The present invention attempts to provide an electrosurgical system having a surgical instrument that can be used in more than one manner, so as to reduce the number of times that an alternative instrument needs to be used.

Accordingly, an electrosurgical system is provided for the treatment of tissue, the electrosurgical system comprising an electrosurgical generator for generating a radio frequency (RF) voltage, and an electrosurgical instrument for the vaporisation of tissue, the instrument comprising an instrument shaft having a longitudinal axis, and an electrode assembly at one end of the shaft, the electrode assembly comprising a tissue treatment electrode and a return electrode electrically insulated one from another by means of an insulation member, the tissue treatment electrode having an exposed surface for treating tissue, the exposed surface of the tissue treatment electrode being laterally disposed with respect to the instrument shaft, and being such that it presents a substantially planar face lying in a plane angled at between 120° and 177.5° to the longitudinal axis, with 0° and 180° being the proximal and distal directions of the longitudinal axis, the generator being such that the magnitude of the RF voltage delivered to the tissue treatment electrode is sufficient to cause tissue vaporisation when the system is used for tissue treatment.

The planar face of the tissue treatment electrode lies at an angle such that it presents a rearwardly facing surface as compared with the longitudinal axis of the shaft. This allows the instrument to be used in a manner in which the instrument is retracted against tissue to be treated. This is a technique which is familiar to surgeons, and allows for good control of the instrument as it is pulled rearwardly towards the user. Instruments that allow for a retracting method of use are known in the form of hook-shaped instruments, but the present invention provides the considerable advantage of providing a planar surface capable of the bulk removal or the coagulation of tissue.

In one convenient arrangement, the instrument shaft has a proximal portion and a distal portion, the proximal portion being on the longitudinal axis, and the distal portion being at an angle to the longitudinal axis. Thus, the shaft is angled towards its distal end, the angle of the distal portion typically being between 2.5° and 45° to the longitudinal axis. The tissue treatment electrode is conveniently laterally disposed on the distal portion of the shaft such that its substantially planar face lies parallel to the axis of the distal portion of the shaft. In this way, the planar face of the tissue treatment electrode is at the same angle as the distal portion of the shaft, thereby providing the rearward angle to allow for the instrument to be retracted in use.

In an alternative arrangement, the instrument shaft is substantially straight along its entire length, and the tissue treatment electrode is mounted at an angle to the longitudinal axis of the shaft. By mounting the tissue treatment electrode at an angle with respect to the shaft, a backward rake is provided without requiring the shaft to be angled appropriately. In a preferred arrangement, the tissue treatment electrode has a wedge-shaped structure. Typically, the wedge-shaped tissue treatment electrode has a first face parallel to the instrument shaft, and a second face at an angle of between 2.5° and 45° to the first face. This triangular cross-section allows a backward rake to be provided for the planar face of the tissue treatment electrode, while the attachment to the instrument shaft is simplified by the parallel first face of the electrode.

In a further preferred arrangement, the electrosurgical instrument includes both first and second return electrodes, the first return electrode being located at a shorter distance from the tissue treatment electrode than the second return electrode. This allows for the selection of the optimal return electrode depending on whether tissue vaporisation or tissue coagulation is desired. Accordingly, the electrosurgical generator preferably comprises a source of radio frequency energy capable of producing either a coagulating RF waveform or a cutting RF waveform, and first, second and third output connections connected to the tissue treatment and the first and second return electrodes respectively of the electrosurgical instrument, the generator further comprising a switching means and a controller, the controller being such that, when a cutting RF waveform is selected, the switching means directs the cutting RF waveform between the first and second output connections and hence between the tissue treatment electrode and the first return electrode; and, when a coagulating RF waveform is selected, the switching means directs the coagulating RF waveform between the first and third output connections and hence between the tissue treatment electrode and the second return electrode. In this way, the first return electrode is employed when the tissue treatment electrode is performing tissue vaporisation, and the second return electrode is employed when the tissue treatment electrode is performing tissue coagulation.

This electrosurgical system includes the switch means by which the surgeon can select either the cutting RF waveform or the coagulating RF waveform modes of operation. Conveniently, the switch means comprises a footswitch, although as an alternative the switch means conceivably comprises a handswitch carried on the electrosurgical instrument. Alternatively, the switch means can be located on the generator. The switch means activates the switching circuit, which is conveniently a part of the generator, although as an alternative the switching circuit is conceivably a part of the electrosurgical instrument.

According to a preferred arrangement, the second return electrode is set back axially with respect to the tissue treatment electrode. This is conveniently achieved by positioning the tissue treatment electrode at the extreme distal end of the instrument. Conveniently, the second return electrode is in the form of a metallic sheath provided on the instrument shaft.

According to another aspect of the invention, the tissue treatment electrode has first and second exposed planar surfaces for treating tissue, the first exposed surface being such as to treat tissue disposed on the longitudinal axis, and the second exposed surface being such as to treat tissue disposed laterally of the longitudinal axis. Conveniently, the tissue treatment electrode comprises a single electrode structure located at the distal end of the instrument shaft so as to extend across at least part of the end face of the instrument to form the first exposed surface, the tissue treatment electrode also extending around the edge of the end face of the instrument in at least one region thereof so as to form the second exposed surface. The surface area of one of the exposed surfaces is typically at least 2 mm$^2$ and the surface area of the other exposed surface is typically at least 0.5 mm$^2$.

Preferably, where the electrode is a wedge-shaped tissue treatment electrode, the tissue treatment surface extends around the distal end of the instrument so as to provide the ability for the instrument to treat tissue adjacent both areas. By providing an electrosurgical instrument that can treat tissue disposed on the longitudinal axis (an "end-effect instrument"), as well as treating tissue laterally of said longitudinal axis (a "side-effect instrument") the present invention allows a surgeon to perform different surgical actions with the same instrument, as opposed to withdrawing a first instrument and inserting a second.

The backward rake presented by the planar surface of the tissue treatment electrode can be at any convenient angle within the above described range, but the exposed surface of the tissue treatment electrode is such that it presents a substantially planar face lying in a plane angled at conveniently between 135° and 170° and preferably between 150° and 165° to the longitudinal axis.

In order to provide aspiration of vaporised tissue, a suction lumen is preferably provided, extending along the length of the shaft. The tissue treatment electrode is conveniently provided with at least one aperture in communication with the suction lumen, to allow tissue vaporised by the tissue treatment electrode to be aspirated via the suction lumen. Conceivably, the lumen could additionally or alternatively be used for the supply of fluid to the distal end of the instrument.

In a first arrangement, the generator and electrosurgical instrument are such that the instrument is operable in a conductive fluid, with the conductive fluid completing the current path between the electrodes. This means that the system operates to perform what is known as "underwater" electrosurgery, in which the conductive site is immersed in a conductive fluid such as saline, and the electrodes operate immersed in said conductive fluid. An example of this type of electrosurgical system is given in our earlier U.S. Pat. No. 6,004,319. The power and voltage setting used by the generator are such that the conductive fluid surrounding the electrodes is vaporised when the electrosurgical instrument is operated in its cutting mode.

Alternatively, the generator and electrosurgical instrument are such that the instrument is operable in a dry-field environment, with the electrodes being in direct contact with the tissue to be treated, and with the tissue completing the current path therebetween. An example of this type of electrosurgical system is given in our earlier U.S. Pat. No. 6,832,998. The power and voltage settings used by the generator are generally lower than in underwater electrosurgical systems, as the electrodes contact the tissue directly and there is no need to form a pocket of vaporised saline surrounding the electrode.

According to a further aspect of the present invention, there is provided an electrosurgical instrument for the treatment of tissue, the instrument comprising an instrument shaft having a longitudinal axis, and an electrode assembly at one end of the shaft, the electrode assembly comprising a tissue treatment electrode and a return electrode electrically insulated one from another by means of an insulation member, the tissue treatment electrode having first and second exposed planar surfaces for treating tissue, the first exposed surface being such as to treat tissue disposed on the longitudinal axis, and the second exposed surface being such as to treat tissue disposed laterally of the longitudinal axis, the tissue treatment electrode comprising a single electrode structure located at the distal end of the instrument shaft so as to extend across at least part of the end face of the instrument to form the first exposed surface, the tissue treatment electrode also extending around the edge of the end face of the instrument in at least one region thereof so as to form the second exposed surface, the surface area of one of the exposed surfaces being at least 2 mm$^2$ and the surface area of the other exposed surface being at least 0.5 mm$^2$.

By extending the tissue treatment electrode around the distal end of the instrument, it can operate as both a side-effect instrument and also as an end-effect instrument as previously described. The surface area of the first exposed surface conveniently at least 0.5 mm$^2$ and the surface area of the second exposed surface is at least 2 mm$^2$.

The electrosurgical instrument preferably includes both first and second return electrodes as previously described, the first return electrode being located at a shorter distance from the tissue treatment electrode as compared with the second return electrode. This allows the desired return electrode to be selected depending on the intended function of the instrument, also as previously described.

Figure 2:
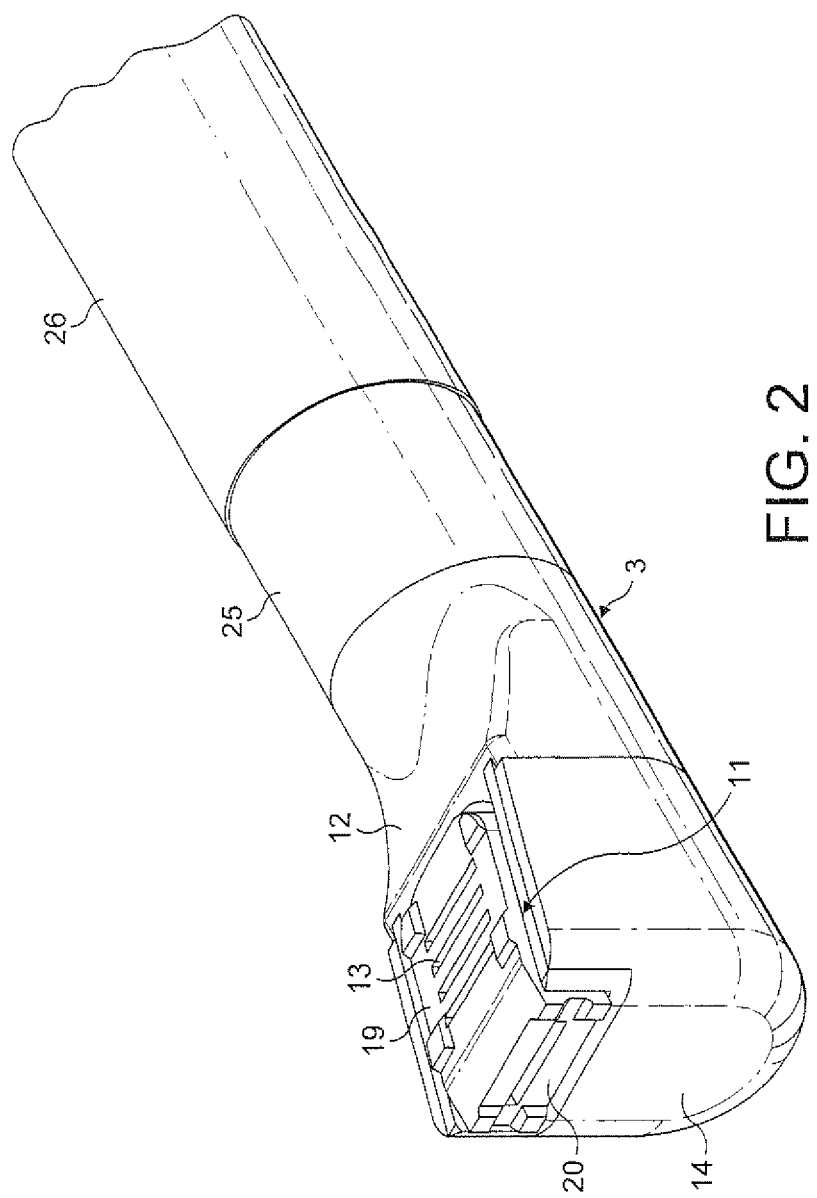
Figure 3:
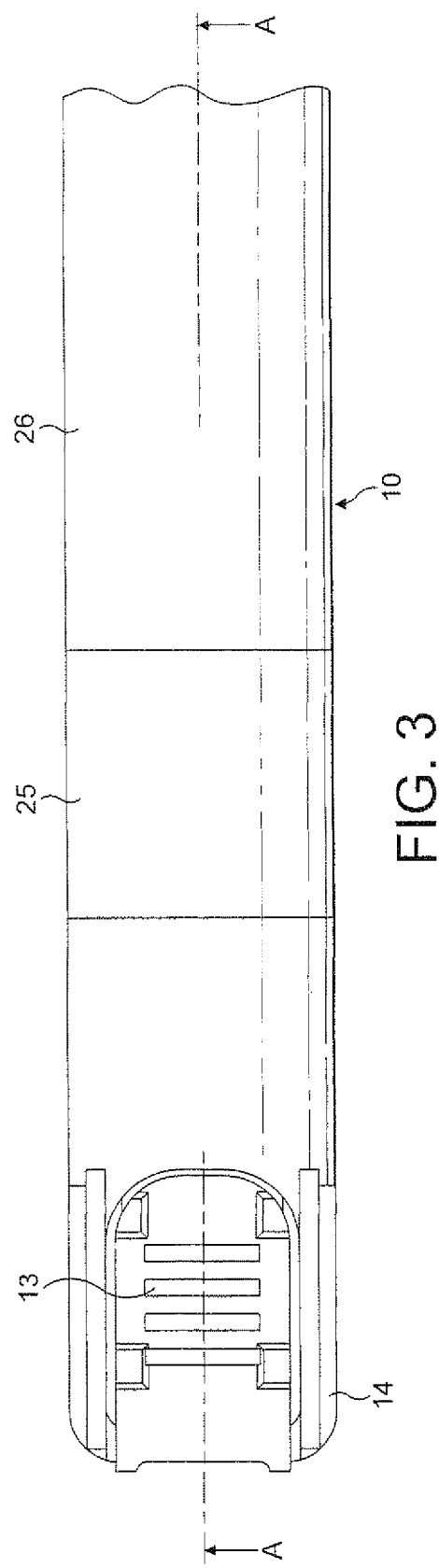
Figure 4:
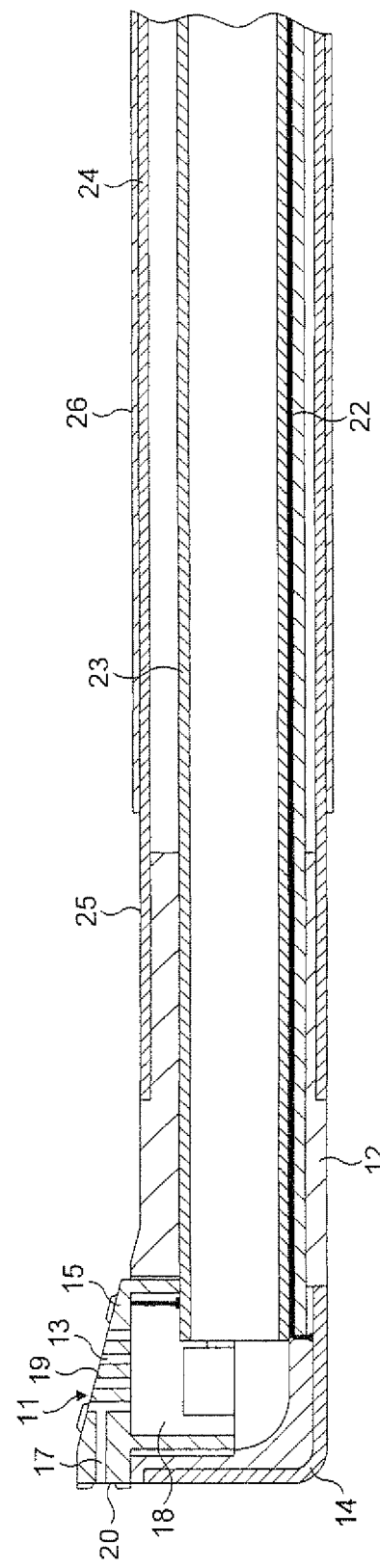
Figure 5A:
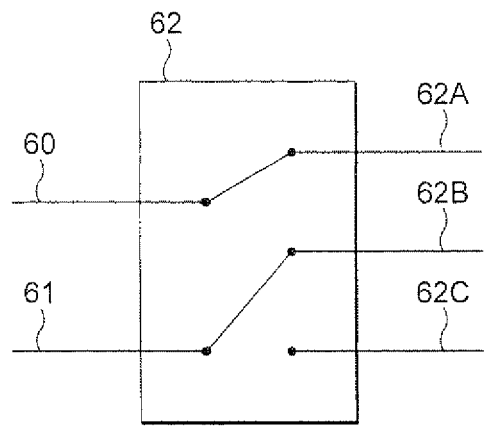
Figure 5B:
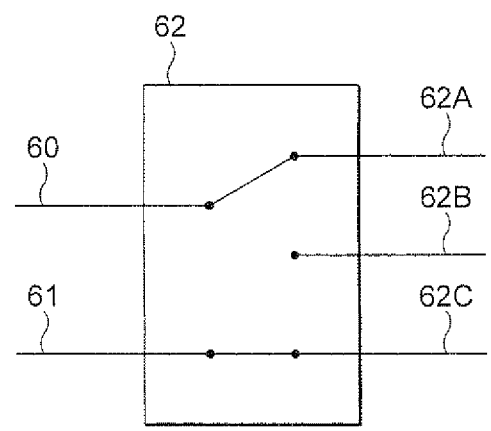
Figure 6:
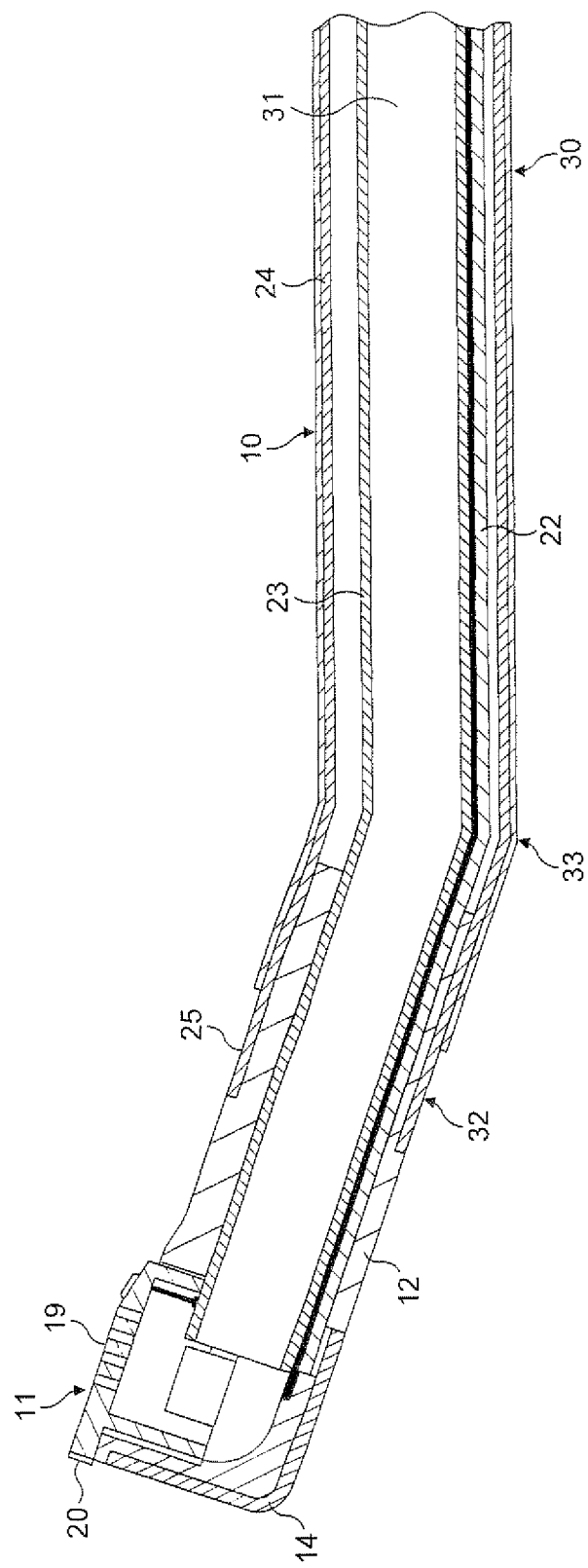
Figure 7:
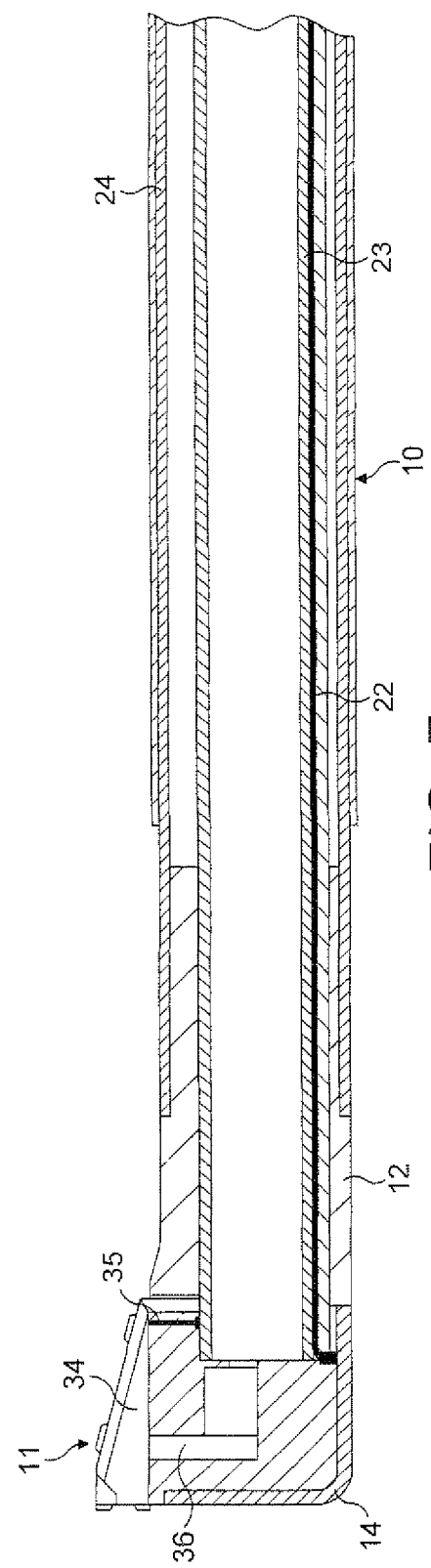

The invention will now be further described, by way of example only, with reference to the drawings, in which:

FIG. 1 is a schematic diagram of an electrosurgical system constructed in accordance with the present invention, FIG. 2 is a perspective view of an electrosurgical instrument constructed in accordance with the present invention, and capable of being used in the system of FIG. 1, FIG. 3 is a plan view of the electrosurgical instrument of FIG. 2, FIG. 4 is a cross-section of the electrosurgical instrument of FIG. 3, taken along the line A-A, FIGS. 5A and 5B are schematic block diagrams of the output stage of the electrosurgical generator of FIG. 1, shown in different stages of operation, FIG. 6 is a cross-section of an alternative embodiment of instrument to that of FIG. 4, and FIG. 7 is a cross-section of a further alternative embodiment of instrument to that of FIG. 4.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

The handpiece 3 comprises a straight shaft 10 with electrodes at its distal end, as will be described below. FIGS. 2 to 4 show a tissue treatment electrode 11 mounted on a ceramic insulator 12, this electrode comprising an upper portion 15, and a lower portion 18 which serves to locate the electrode within the insulator 12. The upper portion 15 includes a first tissue treatment surface 19 and a second tissue treatment surface 20. The upper portion 15 of the electrode 11 is generally wedge-shaped, such that the first tissue treatment surface 19 is presented at an angle of approximately 30° with respect to the longitudinal axis of the shaft 10. The surface 19 is angled such that it presents an inclined surface as it progresses towards the distal end of the shaft 10. The surface area of the first tissue treatment surface 19 may be at least 2 mm$^2$, and the surface area of the second tissue treatment surface 20 may be at least 0.5 mm$^2$.

The second tissue treatment surface 20 is provided at the distal end face of the upper portion 15, being constituted by the thick end of the wedge-shaped upper portion 15. The tissue treatment electrode 11 is formed of tungsten or an alloy of tungsten and platinum. The tissue treatment electrode 11 is provided with suction apertures 13 and 17, the apertures 13 being provided in the first tissue treatment surface 19, and the apertures 17 being provided in the second tissue treatment surface 20. The suction apertures 13 and 17 are in communication with a suction tube 23 extending along the shaft 10. In order to reduce the problems of vapour bubble production, and to assist with the removal of particulate material (such as tissue debris) from the region surrounding the tissue treatment electrode 11, the suction tube 23 is connected to a suction pump (not shown) which can remove vapour bubbles via the shaft of the instrument through the apertures 13 and 17. The suction tube 23 is formed of an electrically-conductive material, and acts as a lead connecting the tissue treatment electrode 11 to the RF generator 1 of FIG. 1. The lower portion 18 of the electrode 11 is in contact with the suction tube 23, to form a connection between the tube and the electrode.

A first return electrode 14 is provided at the distal end of the shaft 10 adjacent to the tissue treatment electrode 11, and extends around both sides of the distal end of the shaft. A second return electrode 25 is provided by the distal end portion of the shaft 10. A polytetrafluoroethylene, a polyolefin, a polyester or ethylene tetrafluoroethylene sleeve 26 surrounds the proximal portion of the shaft 10 adjacent to the return electrode 25. Leads 22 and 24 connect the electrodes 14 and 25 to the RF generator 1 shown in FIG. 1.

The RF generator 1 delivers an electrosurgical current to the instrument 3. The generator 1 includes means for varying the delivered output power to suit different electrosurgical requirements, such as vaporisation or coagulation. The generator 1 is typically as described in our earlier U.S. Pat. No. 6,293,942, with a switching circuit 62 (see FIGS. 5A and 5B) for switching the output lines from the generator to the electrosurgical instrument 3.

The switching circuit 62 comprises connections 60 and 61 from the generator 1, and output connections 62A, 62B and 62C respectively. The output connection 62A is connected to the tissue treatment electrode 11 via the suction tube 23, while the output connection 62B is connected to the first return electrode 14 via the lead 22. Similarly, the output connection 62C is connected to the second return electrode 25, via the lead 24. The operation of the electrosurgical system will now be described.

When the user of the system wishes to use the instrument 3 as a tissue cutting instrument, the user sends signals (via the footswitch unit 5 or via the push buttons 9 on the generator 1) to set the switching circuit 62 into the condition shown in FIG. 5A. In this condition, the connections 60 and 61 from the generator 1 are connected to the output connections 62A and 62B, and hence to the tissue treatment electrode 11 and the first return electrode 14 respectively. RF power from the generator 1 is supplied to the electrodes 11 and 14, and hence tissue can be vaporised as desired at the end of the shaft 10. The first tissue treatment surface 19 acts as a side-effect electrode, with the inclined face allowing the user to retract the instrument against tissue to be vaporised. The second tissue treatment surface 20 acts as an end-effect electrode, allowing the user to vaporise tissue adjacent to the end of the instrument. The first return electrode 14 acts as the return electrode for both the first and second tissue treatment surfaces 19 and 20.

Alternatively, when the user of the system wishes to use the instrument 3 as a tissue coagulating instrument, the user sends signals to set the switching circuit 62 into the condition shown in FIG. 5B. In this condition, the connections 60 and 61 from the generator 1 are connected to the output connections 62A and 62C, and hence to the tissue treatment electrode 11 and the second return electrode 25 respectively. RF power from the generator 1 is supplied to the electrodes 11 and 25, and hence tissue can be coagulated as desired. As before, the first tissue treatment surface 19 acts as a side-effect electrode, with the inclined face allowing the user to retract the instrument against tissue to be coagulated. The second tissue treatment surface 20 acts as an end-effect electrode, allowing the user to coagulate tissue adjacent to the end of the instrument. The second return electrode 25 acts as the return electrode for both the first and second tissue treatment surfaces 19 and 20.

The instrument 3 is designed to be operated in a conductive fluid such as saline, with the fluid completing the circuit between the electrodes. However, the instrument 3 can also be used as a dry-field instrument, in which case the user must ensure that the electrodes are placed in contact with the tissue to be treated.

Alternative embodiments will be envisaged by those skilled in the art without departing from the scope of the present invention. For example, the electrosurgical instrument can also be used for delivering a blended power output. This is achieved by automatically alternating the output of the RF generator 1 between the coagulation and vaporisation power levels, so that more haemostasis is produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the coagulation mode. This produces a less aggressive tissue vaporisation than occurs in the vaporisation mode, with a consequent reduction in both bubble formation and the risk of tissue charring.

FIG. 6 shows an alternative design of the instrument 3, in which the shaft 10 is provided with a proximal portion 30 extending along a longitudinal axis 31, and a distal portion 32 extending at an angle of approximately 30° to the axis 31. The distal portion 32 may extend at an angle of between 2.5° and 45° to the longitudinal axis of the instrument 3. An elbow portion 33 constitutes the junction between the proximal portion 30 and the distal portion 32. The tissue treatment electrode 11 is located on the side of the distal portion and is substantially planar as opposed to the wedge-shaped electrode shown in FIGS. 2 to 4. The electrode 11 has a tissue treatment surface 19 which is inclined with respect to the longitudinal axis 31. As before, the electrode 11 also provides a second tissue treatment surface 20 on the end of the instrument. First and second return electrodes 14 and 25 are situated as previously described.

The operation of the instrument 3 is substantially as previously described, with the tissue treatment electrode 11 offering a backwardly-angled tissue treatment surface 19 to allow the user to retract the instrument against tissue. The angle of the distal portion 32 with respect to the proximal portion 30 provides the backward rake, without requiring a wedge-shaped electrode.

FIG. 7 shows a further design of instrument, in which the shaft 10 is substantially straight, and in which the electrode 11 is mounted at an angle to the axis 31 by means of an angled spacer 34 forming part of the ceramic insulator 12. The electrode 11 is connected to a conductive suction tube 23 by means of a lead 35, and the spacer 34 includes one or more apertures 36 to allow for suction through the electrode 11. As before, this allows the electrode 11 to present a tissue treatment surface 19 at an angle to the axis 31, without requiring either an angled shaft or a wedge-shaped electrode. However, the advantage is still the same, in that the instrument can be retracted against tissue in a rearward motion, with the backward rake of the tissue treatment surface 19 providing greater control of the instrument.

In each of the embodiments, the first tissue treatment surface 19 presents a substantially planar face lying in a plane angled at between 120° and 177.5° to the longitudinal axis of the instrument 3, with 0° and 180° being the proximal and distal directions of the longitudinal axis.

The invention claimed is:

1. An electrosurgical system comprising an electrosurgical generator for generating a radio frequency (RF) voltage, and an electrosurgical instrument for the vaporisation of tissue, the instrument comprising an instrument shaft having a longitudinal axis, the instrument shaft being substantially straight along its entire length, and an electrode assembly at one end of the shaft, the electrode assembly comprising a tissue treatment electrode and a return electrode electrically insulated one from another by means of an insulation member, the tissue treatment electrode having first and second exposed planar surfaces for treating tissue, the first exposed surface being such as to treat tissue disposed on the longitudinal axis, and the second exposed surface being such as to treat tissue disposed laterally of the longitudinal axis, the second exposed surface of the tissue treatment electrode being such that it presents a substantially planar face lying in a plane angled at between 120° and 177.5° to the longitudinal axis, with 0° and 180° being the proximal and distal directions of the longitudinal axis, the generator being such that the magnitude of the RF voltage delivered to the tissue treatment electrode is sufficient to cause tissue vaporisation when the system is used for tissue treatment.

2. An electrosurgical system according to claim 1, wherein the tissue treatment electrode is mounted at an angle to the longitudinal axis of the shaft.

3. An electrosurgical system as claimed in claim 2, wherein the tissue treatment electrode is substantially planar, and is mounted on an angled spacer.

4. An electrosurgical system according to claim 1, wherein the tissue treatment electrode has a wedge-shaped structure.

5. An electrosurgical system according to claim 4, wherein the wedge-shaped tissue treatment electrode has a first face parallel to the instrument shaft and a second face at an angle of between 2.5° and 45° to the first face.

6. An electrosurgical system according to claim 1, wherein the electrosurgical instrument includes both first and second return electrodes, the first return electrode being located at a shorter distance from the tissue treatment electrode than the second return electrode.

7. An electrosurgical system according to claim 6, wherein the electrosurgical generator includes a source of radio frequency energy capable of producing either a coagulating RF waveform or a cutting RF waveform, and first, second and third output connections connected to the tissue treatment and the first and second return electrodes respectively of the electrosurgical instrument, the generator further comprising a switching means, and a controller, the controller being such that, when a cutting RF waveform is selected, the switching means directs the cutting RF waveform between the first and second output connections and hence between the tissue treatment electrode and the first return electrode; and, when a coagulating RF waveform is selected, the switching means directs the coagulating RF waveform between the first and third output connections and hence between the tissue treatment electrode and the second return electrode.

8. An electrosurgical system according to claim 1, wherein the instrument includes an end face, and the tissue treatment electrode comprises a single electrode structure located at the distal end of the instrument shaft so as to extend across at least part of the end face of the instrument to form the first exposed surface, the tissue treatment electrode also extending around the edge of the end face of the instrument in at least one region thereof so as to form the second exposed surface.

9. An electrosurgical system according to claim 8, wherein, the surface area of one of the exposed surfaces is at least 2 mm$^2$, and the surface area of the other exposed surface being at least 0.5 mm$^2$.

10. An electrosurgical system according to claim 1, wherein the exposed surface of the tissue treatment electrode is laterally disposed on the instrument shaft and being such that it presents a substantially planar face lying in a plane angled at between 135° and 170° to the longitudinal axis.

11. An electrosurgical system according to claim 10, wherein the exposed surface of the tissue treatment electrode is laterally disposed on the instrument shaft, and is such that it presents a substantially planar face lying in a plane angled at between 150° and 165° to the longitudinal axis.

12. An electrosurgical system according to claim 1, wherein the generator and electrosurgical instrument are such that the instrument is operable in a conductive fluid, with the conductive fluid completing the current path between the electrodes.

13. An electrosurgical system according to claim 1, wherein the generator and electrosurgical instrument are such that the instrument is operable in a dry-field environment, with the electrodes being in direct contact with the tissue to be treated, and with the tissue completing the current path therebetween.

* * * * *